US012779072B2

(12) United States Patent
Luo et al.

(10) Patent No.: US 12,779,072 B2
(45) Date of Patent: Nov. 3, 2026

(54) OZONE DISINFECTION DEVICE

(71) Applicant: DCSTAR INC, New York, NY (US)

(72) Inventors: David Luo, New York, NY (US); Ligui He, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 19/027,660

(22) Filed: Jan. 17, 2025

(65) Prior Publication Data

US 2026/0207805 A1 Jul. 23, 2026

(51) Int. Cl.

*A61L 2/202* (2026.01)
*A61L 2/26* (2006.01)
*A61L 103/15* (2026.01)

(52) U.S. Cl.

CPC ................ *A61L 2/202* (2013.01); *A61L 2/26* (2013.01); *A61L 2103/15* (2026.01); *A61L 2202/11* (2013.01); *A61L 2202/121* (2013.01); *A61L 2202/122* (2013.01); *A61L 2202/14* (2013.01); *A61L 2202/15* (2013.01)

(58) Field of Classification Search

CPC .................................. A61L 2/26; A61L 2/202
See application file for complete search history.

(56) References Cited

U.S. PATENT DOCUMENTS

2016/0235876 A1* 8/2016 Leyva .................... A61L 2/202

FOREIGN PATENT DOCUMENTS

WO WO-2013012696 A1 * 1/2013 .............. A61L 2/24
WO WO-2020191194 A1 * 9/2020 ............ A61L 9/015

* cited by examiner

*Primary Examiner* — Sean E Conley
(74) *Attorney, Agent, or Firm* — HSML P.C.

(57) ABSTRACT

An ozone disinfection device configured to connect with a hose or respiratory-related equipment for disinfection. Specifically, an ozone disinfection device is disclosed that improves safety and reliability during use. The device includes an ozone operation system and a housing. The housing includes a plurality of housing walls and at least one receiving slot and at least one ozone outlet. Additionally, the ozone disinfection device features at least one joint component configured to seal the receiving slot. The sealing of the receiving slot can be achieved in two forms. Furthermore, the ozone operation system has at least an ozone generator, an ozone distribution pipeline, and at least one fan or pump. All three components are configured to be housed within a single chamber formed by the housing of the ozone disinfection device.

21 Claims, 20 Drawing Sheets

OZONE DISINFECTION DEVICE

TECHNICAL FIELD

The present disclosure relates to an ozone disinfection device configured for disinfecting respiratory-related equipment and its accessories. The device is configured to distribute ozone into the pipelines connected to respiratory-related equipment and/or its accessories, delivering ozone for cleaning and disinfection purposes.

BACKGROUND

One of the primary causes of sleep apnea is the relaxation of soft tissues in the throat, particularly in the soft palate area located at the back of the upper oral cavity. When awake, muscles are generally tense, which keeps the airway open and unobstructed. However, during deep sleep, these muscles begin to relax, especially the soft tissues in the throat. This can lead to partial airway blockage and vibration, resulting in snoring. If the blockage becomes severe, it may progress to sleep apnea. Relaxed muscles also narrow the upper airway, increasing the frequency of vibrations and exacerbating both snoring and the severity of sleep apnea. Symptoms such as breathing pauses during sleep should prompt early examination and treatment. Currently, there are several treatment methods for sleep apnea. Weight loss therapy can help reduce the incidence of apnea and hypopnea, particularly in overweight individuals, though it may not resolve or alleviate symptoms for everyone. Continuous positive airway pressure (CPAP) therapy uses a breathing machine to deliver air at a constant pressure, helping to expand the airway and is suitable for moderate to severe OSA (obstructive sleep apnea) patients. Oral appliance therapy involves using a device to stabilize the upper and lower dental arches, moving the lower jaw forward to expand the airway. Surgical treatments, such as uvulopalatopharyngoplasty (UPPP), orthognathic surgery, and tracheostomy, aim to reduce or eliminate airway obstructions. Choosing the appropriate treatment method based on the severity of sleep apnea and individual preferences is essential for improving sleep quality, reducing the risk of related complications, and enhancing overall quality of life.

Continuous positive airway pressure (CPAP) therapy is the most widely accepted and preferred treatment method. The components required for CPAP include a CPAP device (i.e., a ventilator), tubing, a mask, and a headband. The mask typically consists of a support structure and a sealing part and is available in various designs to accommodate different user needs and comfort levels. These include nasal pillows, nasal masks, full-face masks, and oral-nasal masks. Selecting the appropriate mask type, which depends on factors such as sleeping posture, facial structure, and personal preferences, can significantly impact the effectiveness of CPAP therapy.

Ozone, as a powerful oxidant, is highly effective in eliminating bacteria, viruses, fungi, and other microorganisms, achieving deep cleaning, and is particularly suited for ventilatory devices with hard-to-clean interiors. After cleaning with ozone, the gas eventually decomposes into oxygen, leaving no harmful chemical residues. This makes ozone cleaning more environmentally friendly compared to chemical disinfectants.

Using appropriate disinfection methods can prevent respiratory infections or complications caused by bacteria, fungi, and viruses growing on equipment surfaces, accessories, or internal tubing and being introduced into the user's airway via airflow. For individuals with allergies, the accumulation of dust, pollen, or other allergens in uncleaned tubing can pose a significant risk, potentially triggering respiratory allergies or asthma symptoms. Regular cleaning and disinfection also help reduce odors from the equipment, providing fresher airflow, improving the user experience, and increasing adherence to therapy.

SUMMARY

The present disclosure addresses the aforementioned shortcomings by providing an ozone disinfection device that is user-friendly, reduces user costs, and ensures comfortable operation.

In one embodiment, an ozone disinfection device is provided, configured to connect with a hose or respiratory-related equipment for disinfection. The ozone disinfection device includes an ozone operation system that includes an ozone generator and an ozone distribution pipeline, configured to generate ozone gas and control a flow of the ozone gas; and a housing formed by a plurality of housing walls, in which the housing is configured to form at least two chambers and further includes at least one receiving slot and at least one ozone outlet. The at least one receiving slot is configured to be defined by at least one of the housing walls and/or a joint component, and the joint component is configured to provide a seal for the at least one receiving slot. The at least two chambers include a first chamber and a second chamber, in which the ozone operation system is configured to be provided in the first chamber and is in communication with the second chamber, and the at least one ozone outlet is in communication with both the ozone distribution pipeline and the second chamber.

In one embodiment, the ozone operation system further includes at least one fan or pump, and the fan or pump is configured to expel and/or draw ozone gas.

In one embodiment, the at least one ozone outlet is configured to connect to the housing.

In one embodiment, the at least one receiving slot has a first sealing state or a second sealing state, in which the first sealing state is configured to be closed without an opening, and the second sealing state is configured to be sealed while accommodating a hose.

In one embodiment, the joint component includes at least one sealing element, and the at least one sealing element includes a first sealing element and a second sealing element.

In one embodiment, the ozone operation system further includes at least one ozone sensor.

In another embodiment, an ozone disinfection device is provided, configured to connect with a hose or respiratory-related equipment for disinfection. The ozone disinfection device includes an ozone operation system that includes an ozone generator and an ozone distribution pipeline, configured to generate ozone gas and control a flow of the ozone gas; and a housing formed by a plurality of housing walls, in which the housing further includes at least one receiving slot and at least one ozone outlet. The at least one receiving slot is configured to be defined by at least one of the housing walls and/or a joint component, and the joint component is configured to include at least one sealing element. The ozone operation system further includes at least one fan or pump, the fan or pump being configured to expel and/or draw ozone gas.

In one embodiment, a state of the fan or pump differs depending on whether the ozone disinfection device is in an open or closed state.

In one embodiment, the fan or pump does not operate when the ozone disinfection device is in a non-closed state.

In one embodiment, the at least one sealing element includes a first sealing element and a second sealing element, and the ozone disinfection device is configured to selectively use the first sealing element or the second sealing element depending on its operating state.

In one embodiment, at least one of the housing walls and the joint component are configured to form an opening to accommodate the hose.

In one embodiment, the ozone operation system further includes at least one ozone sensor.

In one embodiment, the housing is configured to form at least two chambers.

In yet another embodiment, an ozone disinfection device is provided, configured to connect with a hose or respiratory-related equipment for disinfection. The ozone disinfection device includes an ozone operation system that has an ozone generator and an ozone distribution pipeline, configured to generate ozone gas and control a flow of the ozone gas; and a housing formed by a plurality of housing walls, in which the housing is configured to form at least two chambers and further includes at least one receiving slot and at least one ozone outlet. The at least one receiving slot is at least defined by a joint component. The at least two chambers include a first chamber, in which the ozone operation system is provided in the first chamber, and the ozone operation system further includes at least one fan or pump configured to expel ozone gas from the first chamber and/or draw ozone gas into the first chamber.

In one embodiment, the at least one receiving slot is defined by the joint component and at least one of the housing walls.

In one embodiment, the housing walls further include at least one sealing element configured to seal the hose in conjunction with the joint component.

In one embodiment, the at least one ozone outlet is in communication with the ozone generator.

In one embodiment, the ozone operation system further includes at least one ozone sensor.

In another embodiment, an ozone disinfection device is provided, configured to connect with a hose or respiratory-related equipment for disinfection. The ozone disinfection device includes an ozone operation system that has an ozone generator and an ozone distribution pipeline, configured to generate ozone gas and control a flow of the ozone gas; and a housing formed by a plurality of housing walls, in which the housing further includes at least one receiving slot and at least one ozone outlet. The at least one receiving slot is defined by a joint component and at least one of the housing walls, the housing walls including at least one sealing element. The joint component includes at least one clipping surface that interfaces with the at least one of the housing walls through the at least one sealing element, the at least one sealing element comprising a first sealing element and a second sealing element. The ozone operation system further includes at least one fan or pump, the fan or pump being configured to expel and/or draw ozone gas.

In one embodiment, the at least one ozone outlet is configured to connect to a first end of the hose or directly to the respiratory-related equipment.

In one embodiment, the at least one receiving slot is configured to connect to a second end of the hose.

In one embodiment, the housing forms at least two chambers.

In one embodiment, the ozone disinfection device is configured to selectively use the first sealing element or the second sealing element depending on its operating state.

The ozone disinfection device 1 described in this disclosure provides several notable benefits.

1. Ozone disinfection device is particularly crucial for respiratory-related equipment. Prolonged use of such equipment without regular disinfection or cleaning allows pathogens and bacteria to proliferate rapidly. These microorganisms can enter the human body through the device, posing significant health risks. For devices that require extended and frequent use, periodic disinfection of both the equipment and its accessories is necessary to ensure safe operation. As the demand for respiratory-related equipment increases, the need for compatible ozone disinfection devices will also grow. This disclosure introduces a novel design for ozone disinfection devices, offering users more diversified options. Ozone was selected as the primary disinfection method in this disclosure because of its broad-spectrum sterilization capabilities. Ozone can effectively eliminate a wide range of bacteria, viruses, fungi, and other microorganisms, as well as decompose harmful gases and eliminate odors. This makes ozone highly effective in various scenarios. Compared to other disinfection methods on the market, such as high-temperature or ultraviolet (UV) disinfection, ozone has distinct advantages. High-temperature disinfection requires stringent thermal resistance in device housing to prevent heat damage to internal components, increasing material and design complexity. UV disinfection, on the other hand, is limited by physical obstructions; for effective disinfection, the device must be transparent and free of barriers, which compromises its aesthetics and structural design. Ozone disinfection, by contrast, does not require heating or depend on unobstructed surfaces—only proper sealing is needed for effective operation. This disclosure's ozone disinfection device not only meets users' daily disinfection needs but also surpasses existing devices in terms of sealing performance, enhanced safety, simplified structure, and reduced costs. By addressing current market demands and incorporating innovative design features, this disclosure aims to provide users with a more flexible, convenient, and safe disinfection experience. Further details will be elaborated upon below.

2. This disclosure improves the sealing performance of the receiving slot in the ozone disinfection device, making it more secure and stable. By introducing the joint component as a specialized part, the receiving slot is no longer directly sealed with the upper cover of the ozone disinfection device. Instead, it is defined and/or sealed via at least the joint component. This design differs from existing devices on the market where the receiving slot directly interacts with the upper cover for sealing. It reduces the risk of sealing failure or instability caused by the frequent movement of the upper cover. When the receiving slot is configured to secure one end of a hose, the sealing of the opening between the receiving slot and the hose is not only achieved by the joint component but is also further compressed by the upper cover on the exterior of the joint component. This approach ensures the stability of the connection between the receiving slot and the hose opening. Separating the frequently used components and components for joining, from other components offers additional benefits. When the seal at the opening fails due to prolonged use or other reasons, the issue can be resolved by directly replacing the joint component without needing to replace the upper cover or other integral components. This design makes the ozone disinfection device easier to maintain and reduces maintenance costs.

Furthermore, this method avoids issues related to the upper cover extending into a slender end at the hose connection, which is prone to damage and difficult to seal. Sealing through the joint component instead of directly using the upper cover also enables modularity for the receiving slot. Modularity allows users to select different joint components to accommodate hoses of varying diameters, depending on their needs or the specifications of the device or accessory being disinfected. For manufacturers and retailers, this modular design simplifies inventory management. Different specifications of the joint component can be sold individually or as part of a set to meet diverse user requirements. This design not only offers users a wider range of options but also opens up diversified sales models, enhancing flexibility in both use and distribution.

3. This disclosure equips the ozone disinfection device with a safety system to prevent the overproduction of ozone, which could harm the environment or user health, while adhering to the principles of green design. As a strong oxidant, it is critical to minimize ozone leakage and secondary pollution. High concentrations of ozone can irritate or damage the respiratory tract, eyes, and skin, and prolonged exposure to ozone levels exceeding 0.1 ppm may lead to respiratory system damage. By incorporating a safety system, this disclosure effectively reduces the potential risks of ozone to both the environment and users. Specifically, the ozone disinfection device is configured to ensure that when the upper cover is in a non-closed state, the fan or pump does not operate. This prevents ozone leakage and avoids exposing users or the external environment to high concentrations of ozone gas. In some embodiments, the device also has at least one sensor to monitor the ozone concentration in real time. If the detected ozone concentration exceeds the preset safe range, the ozone disinfection device will immediately cease operation and may even trigger an alarm to alert the user. Additionally, the safety system can include at least one sensor such as a temperature and humidity sensor, oxygen concentration sensor, or current sensor. The at least one sensor ensures that the ozone disinfection device operates under optimal conditions, further enhancing its safety features and providing protection for both users and the environment.

4. This disclosure also proposes connecting the ozone distribution pipeline with the ozone outlet and the second chamber, enabling more precise control of ozone gas and improving the efficiency of the ozone disinfection device. This implementation optimizes the delivery and recovery routes of ozone gas, achieving high disinfection efficiency with the shortest path. Integrating multiple outlets further streamlines the structure of the ozone disinfection device. Compared to existing ozone disinfection devices on the market, this design not only enhances operational efficiency but also significantly improves the overall structure of the device. It reduces the use of complex components and simplifies installation steps, thereby maximizing production efficiency. Additionally, this design substantially lowers the manufacturing and assembly costs of the ozone disinfection device, making it more suitable for large-scale mass production. By using a single three-way pipe to connect the ozone distribution pipeline and the disinfection space, this disclosure reduces the number of pipe connections and minimizes potential leakage risks, thereby enhancing the device's stability and safety. Furthermore, this design facilitates the maintenance and upgrading of the ozone disinfection device, offering users a more convenient and reliable experience.

DETAILED DESCRIPTION

Figure 1:
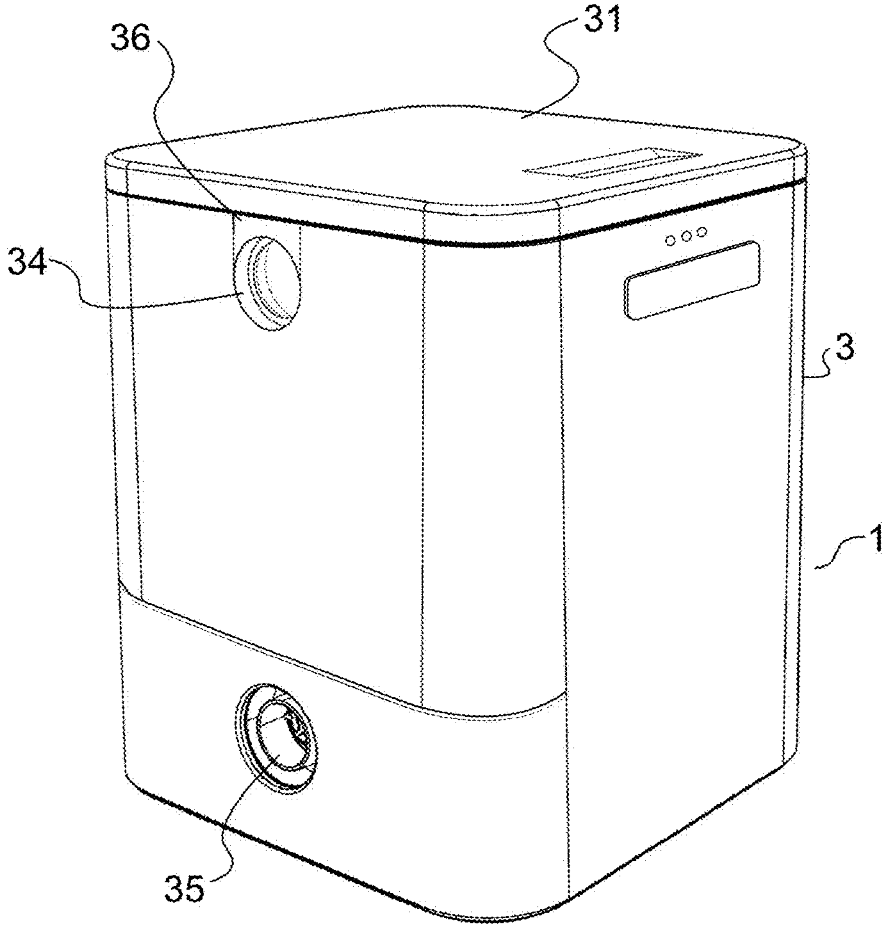
FIG. 1 is a three-dimensional schematic diagram of an ozone disinfection device in accordance with an embodiment of the present disclosure.
Figure 2:
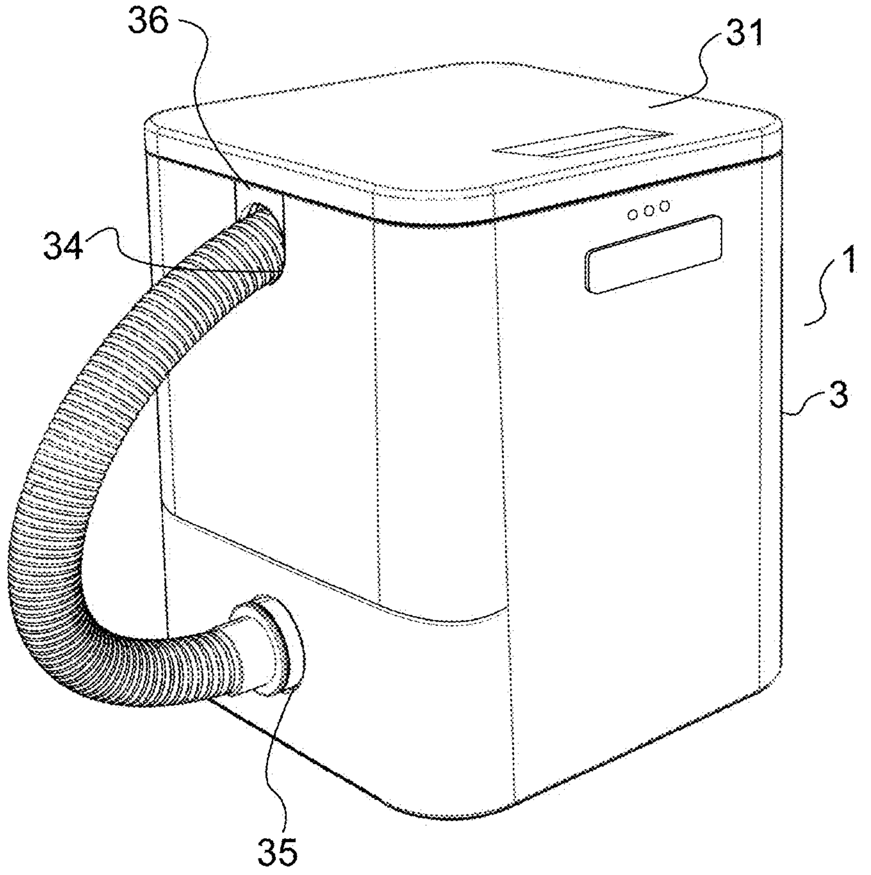
FIG. 2 is a schematic diagram illustrating the use of an ozone disinfection device with a hose in accordance with an embodiment of the present disclosure.

To make the objectives, features, and advantages of this disclosure more apparent and easier to understand, the following provides a detailed explanation of specific embodiments of the disclosure with reference to the accompanying drawings. In the description below, many specific details are provided to facilitate a thorough understanding of the disclosure. However, the disclosure may be implemented in various other ways different from those described herein. Those skilled in the art can make similar modifications without departing from the essence of the disclosure. Therefore, the disclosure is not limited to the specific embodiments disclosed below.

This disclosure involves optimizing the design of an ozone disinfection device 1. Compared to other disinfection devices on the market, such as heat-based disinfection devices and ultraviolet disinfection devices, the ozone disinfection device 1 in this disclosure not only offers unique advantages in sterilization efficiency and application scope but is also more environmentally friendly and safer. Additionally, compared to existing ozone disinfection devices on the market, this disclosure improves at least one receiving slot 34 to enhance its sealing performance and facilitate modularization. These improvements effectively extend the lifespan of ozone disinfection device 1 and enhance its usability. Furthermore, this disclosure provides diversified options for users accustomed to using hoses of different diameters, ensuring the effectiveness and reliability of ozone disinfection device 1 in all aspects. Thus, the ozone disinfection device 1 of this disclosure not only enhances performance metrics but also delivers a more stable, safe, and comfortable user experience.

This disclosure provides an ozone disinfection device 1 that is convenient for users, enhances usability, and ensures safer and more effective operation.

Specifically, as illustrated in FIGS. 1 through 16, the ozone disinfection device 1 of this disclosure includes an ozone operation system 2, which consists of an ozone generator 21 and an ozone distribution pipeline 22, configured to generate ozone gas and control its flow. The device also includes a housing 3 composed of multiple housing walls. The housing 3 forms at least two chambers and includes at least one receiving slot 34 and at least one ozone outlet 35. The at least one receiving slot 34 is defined by at least one housing wall 31 and/or a joint component 36. The ozone operation system 2 is located in the first chamber 32 formed by the housing 3 and communicates with the second chamber 33 formed by the housing 3.

Figure 3:
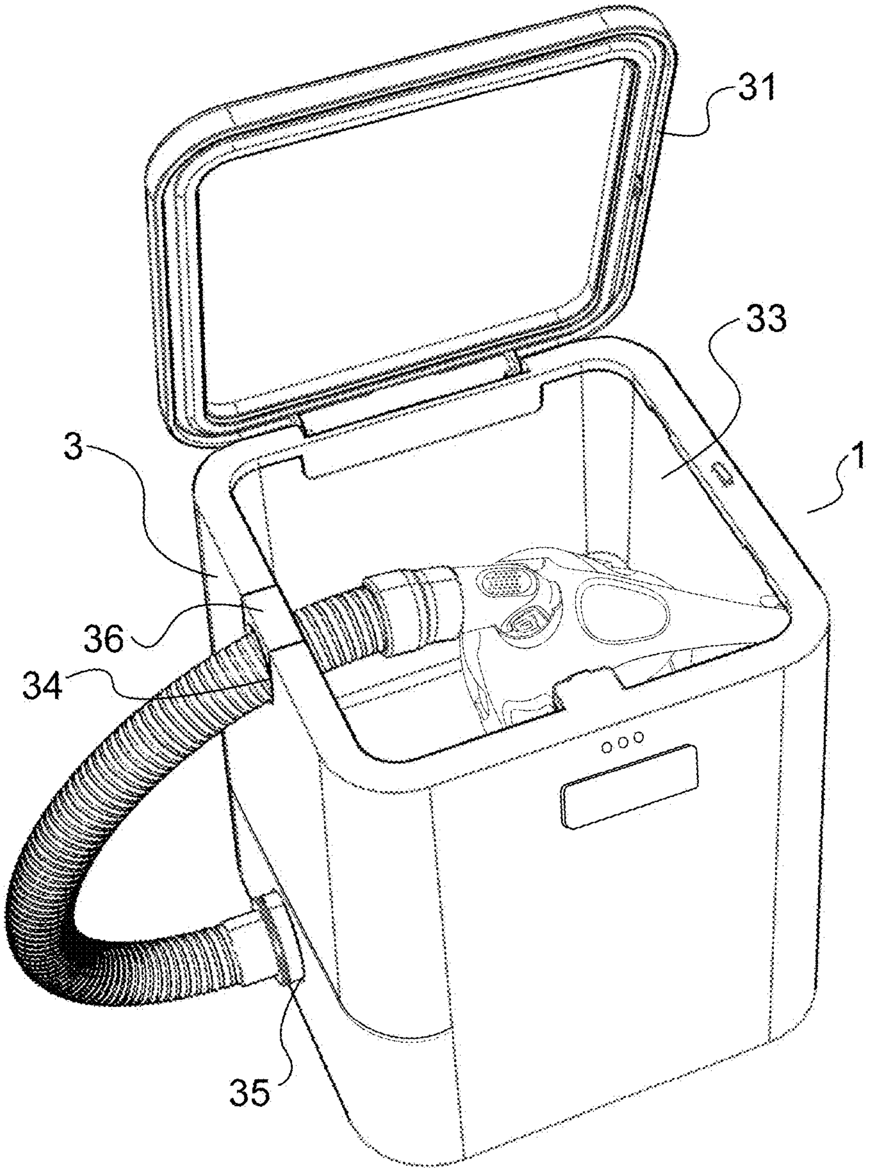
FIG. 3 is a schematic diagram showing the installation and use of an ozone disinfection device in accordance with an embodiment of the present disclosure.
Figure 4:
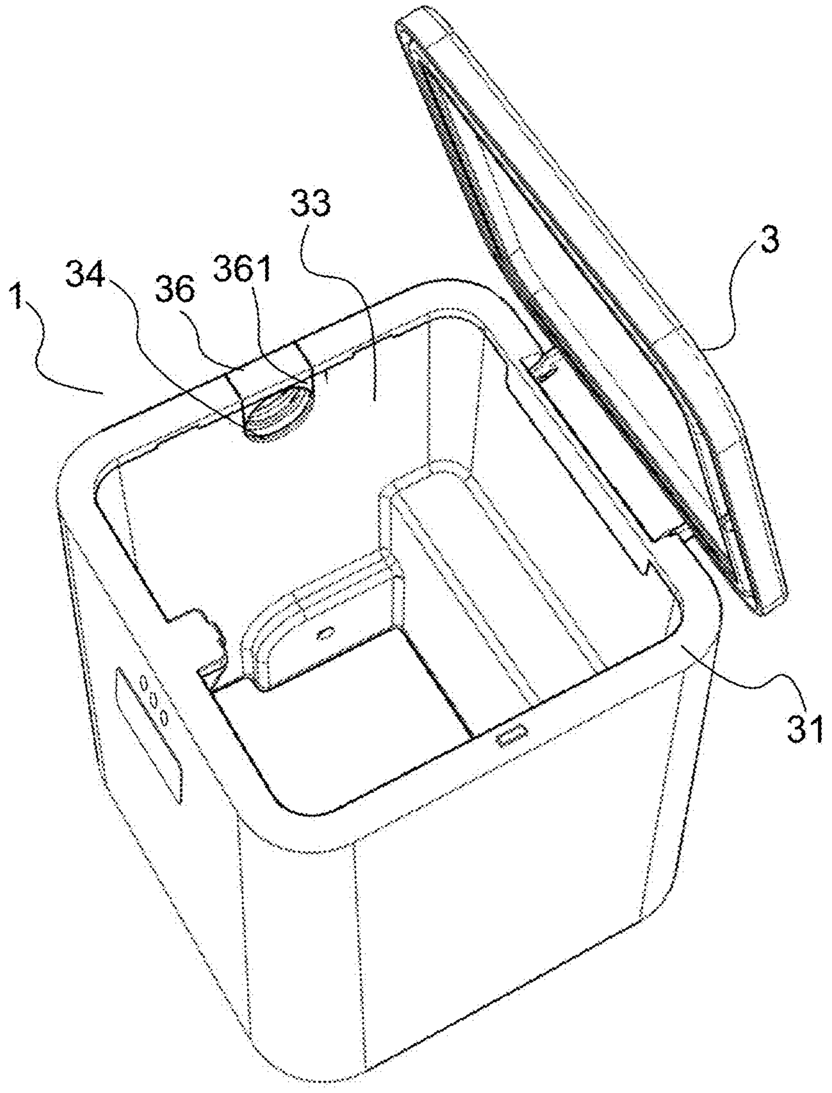
FIG. 4 is a schematic diagram showing the disinfection space (second chamber) of an ozone disinfection device in accordance with an embodiment of the present disclosure.
Figure 16:
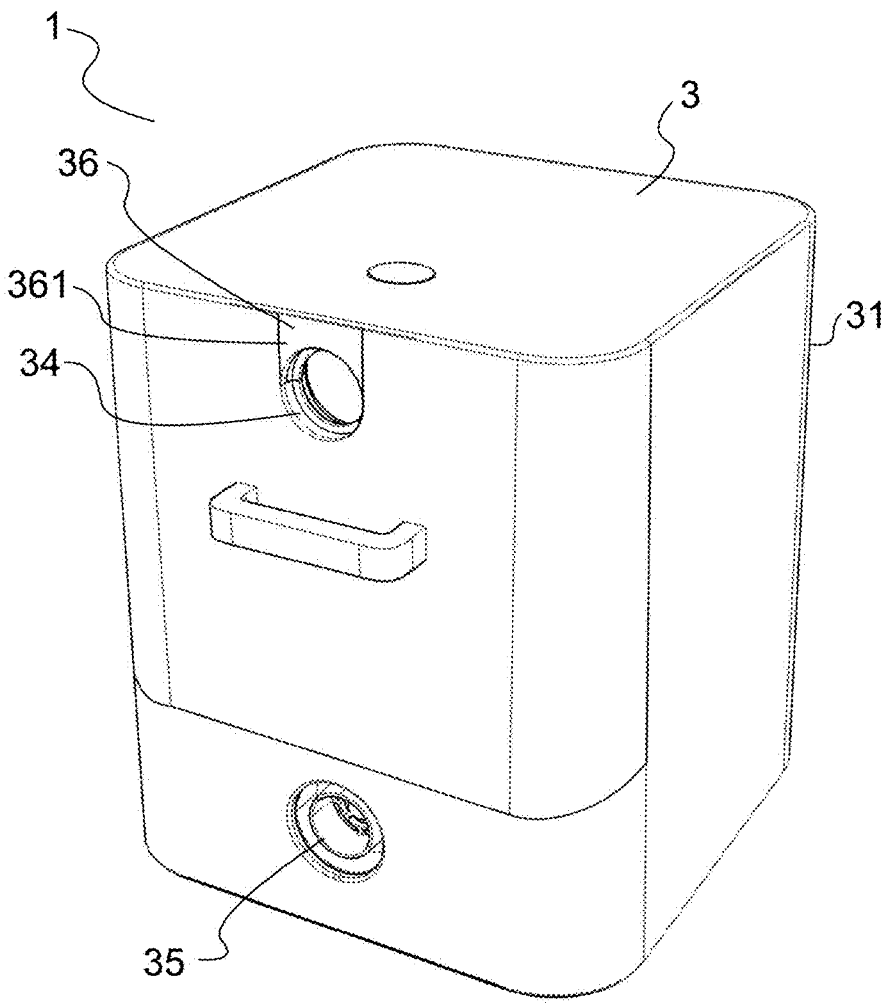
FIG. 16 is a schematic diagram showing the appearance of an ozone disinfection device's housing in a drawer-like form, in accordance with multiple embodiments of the present disclosure.

The ozone disinfection device 1 is fundamentally divided into two main parts: the housing 3 and the internal ozone operation system 2 enclosed by the housing 3. First, in this disclosure, both the overall appearance and the internal space of the ozone disinfection device 1 are defined by the housing 3. The housing 3 is configured to form the ozone disinfection space and to protect its internal components. Additionally, the housing 3 provides structural support for the ozone disinfection device 1, ensuring its stability during use and transportation. The housing 3 is composed of multiple housing walls. In some embodiments, these walls include an upper cover, a lower cover, and surrounding housing walls. The upper cover is configured to be openable (as shown in FIGS. 3 and 4), using mechanisms such as flip-open, sliding, or other methods. In other embodiments, the housing walls may be configured as drawer-like or other forms of enclosures (as illustrated in FIG. 16, showing a drawer-style housing 3 alternative to the flip-open configuration).

Figure 5:
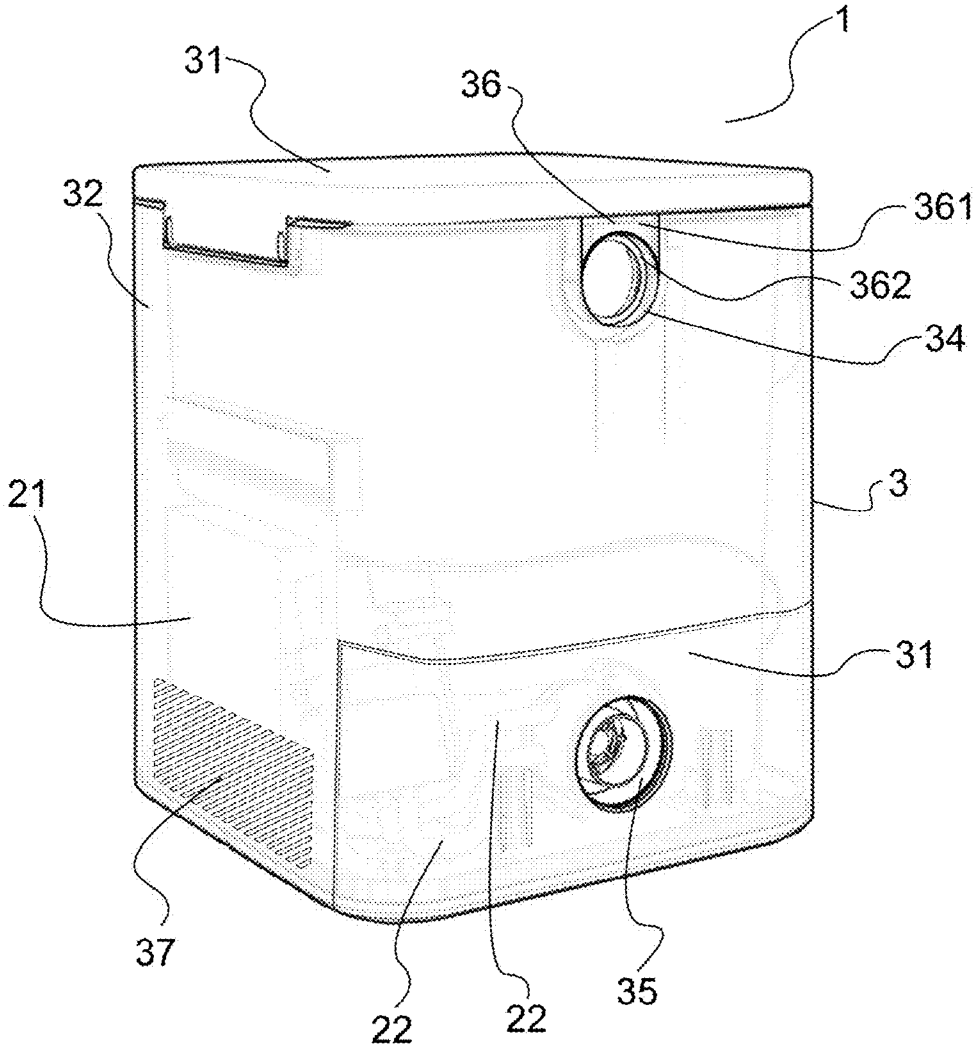
FIG. 5 is a schematic diagram showing the first chamber of an ozone disinfection device and the ozone operation system contained within it, in accordance with an embodiment of the present disclosure.
Figure 6:
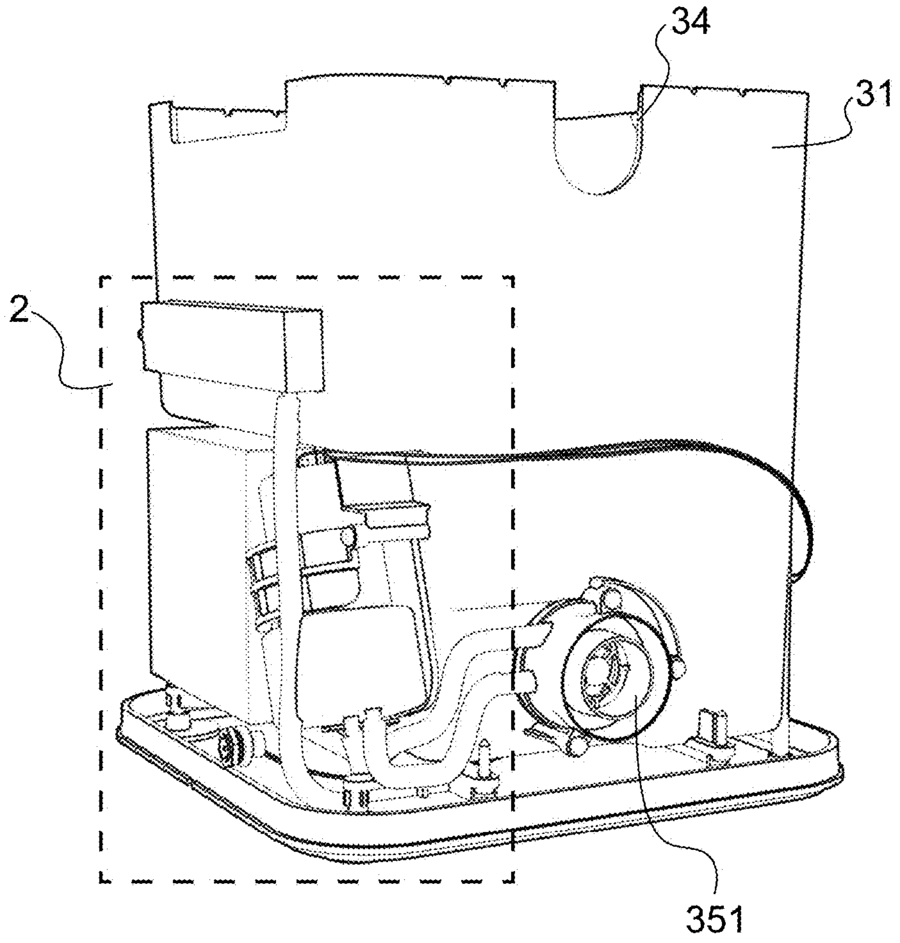
FIG. 6 is a schematic diagram showing the ozone operation system within the first chamber of an ozone disinfection device, in accordance with multiple embodiments of the present disclosure.
Figure 7:
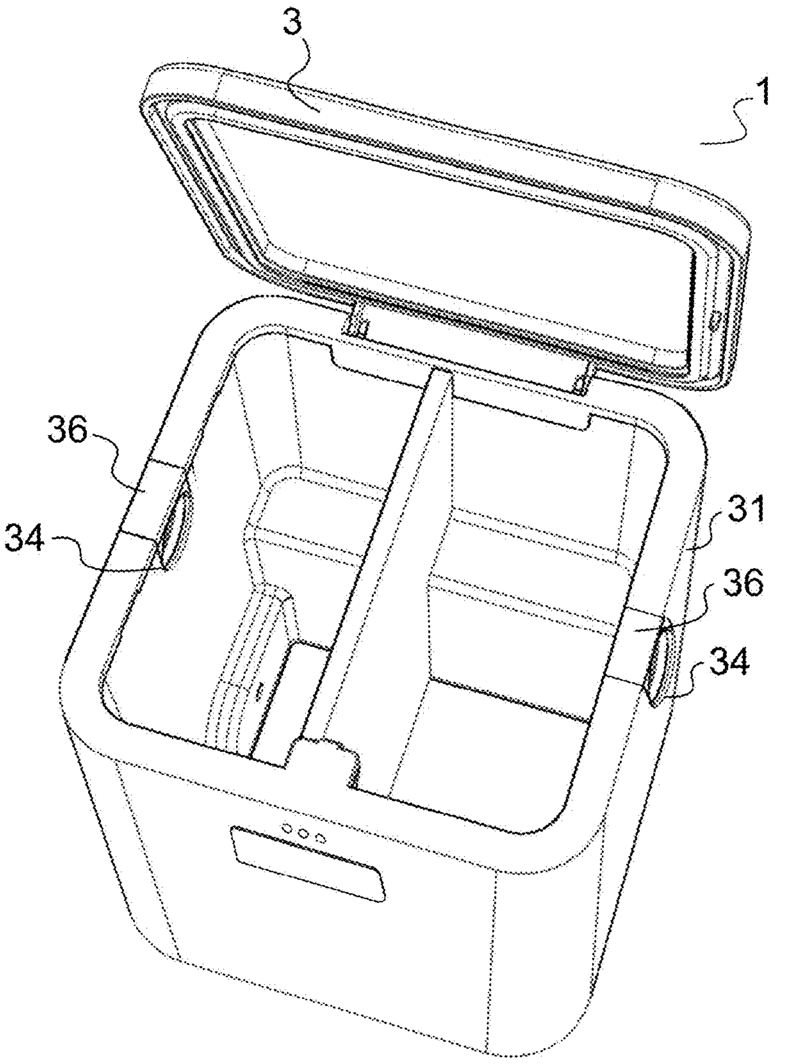
FIG. 7 is a schematic diagram showing an ozone disinfection device with more than two chambers in accordance with an embodiment of the present disclosure.

In this disclosure, the housing 3 forms at least two chambers: one serving as the disinfection space and the other as the space for storing the internal ozone operation system 2. Therefore, the housing 3 of the ozone disinfection device 1 forms at least a first chamber 32 and a second chamber 33. The first chamber 32 houses the internal ozone operation system 2, while the second chamber 33 functions as the disinfection space. Typically, the second chamber 33 (disinfection space) is separated from the first chamber 32 (housing the ozone operation system 2), as shown in FIGS. 4 to 6. This separation is also formed by housing walls. In special cases, the at least two chambers may not be completely separated, resulting in a single chamber design. In such cases, to prevent the ozone gas from harming the internal ozone operation system 2, the external wall of the ozone operation system 2 is made of specially protective materials or structures. Alternatively, the ozone operation system 2 can be enclosed within another space separate from the housing 3. Even with this non-fully separated design, the use of sophisticated wall designs and structural protection ensures that the ozone gas is effectively controlled and directed, maintaining operational safety, reliability, and long-term performance. In other implementations, the housing 3 of the ozone disinfection device 1 may form more than two chambers. For example, the disinfection space chamber may be divided into multiple chambers by partitions, in addition to the chamber for housing the ozone operation system 2. In such cases, the ozone disinfection device 1 may have at least two receiving slots 34 (as shown in FIG. 7). The housing 3 is generally designed as an airtight structure to ensure that ozone gas flows and is stored within the multiple chambers according to the designated pathways and spaces, preventing gas permeation or leakage into the external environment. Additionally, the housing 3 must be corrosion-resistant and made of environmentally friendly materials. Since ozone has highly oxidative properties, the corrosion resistance of the housing 3 ensures the longevity of the device. The materials used to construct the housing 3 of the ozone disinfection device 1 may include, but are not limited to, engineering plastics such as ABS, PC, PPS, PP, metal materials, composite materials, or materials with special coatings or plating. The specific materials for the housing 3 of the ozone disinfection device 1 can be selected based on various factors, including different use scenarios and market demands.

In some embodiments, the housing 3 includes a user interface configured to provide a more convenient operational experience and richer functional feedback for users. The user interface may include, but is not limited to, components such as a display screen, indicator lights, buttons, and interfaces. These components simplify operation and offer more comprehensive functionality indications. The display screen and indicator lights, for example, can show the operating progress of the ozone disinfection device 1, including the percentage of total operating time completed or a countdown of remaining time. They can also indicate parameter settings and fault warning messages, enabling users to clearly understand the device's current operating progress and status. The indicator lights can use different colors or flashing patterns to notify users of the device's status.

In addition to the housing 3, the ozone disinfection device 1 includes an ozone operation system 2, comprising an ozone generator 21 and an ozone distribution pipeline 22. The ozone generator 21, as a core component of the ozone disinfection device 1, is located in the first chamber 32 formed by the housing 3 and is configured to generate ozone gas. Additionally, the first chamber 32 contains at least one fan or pump as part of the ozone operation system 2. The at least one fan or pump is configured to expel and/or draw ozone gas, specifically pushing ozone gas out of the first chamber 32 and/or drawing it into the space of the first chamber 32. In one embodiment of this disclosure, the operational state of the at least one fan or pump varies depending on whether the ozone disinfection device 1 is in a non-sealed or sealed state. For example, when the ozone disinfection device 1 is in a non-sealed state, the at least one fan or pump may remain off. Alternatively, when in a non-sealed state, the at least one fan or pump may operate at a slow speed. This design serves as an effective safety system, helping to control the flow of ozone gas and preventing ozone leakage when the ozone disinfection device 1 is in a non-sealed state, thereby reducing risks to users and the environment. The ozone operation system 2 of the ozone disinfection device 1 may also include at least one filtration device, configured to recover and decompose ozone gas after disinfection. The filtration device contains at least one layer of identical or different filtration materials, and there may be gaps between different filtration layers. Typically, the filtration material contains manganese-based particles to catalyze ozone decomposition. The filtration device can be positioned at any location downstream of the ozone generator 21. Here, "downstream" is defined by the gas flow path, meaning the filtration device can be located at any point where gas flows out from the ozone generator 21. In some embodiments, the filtration device is designed to be upstream of at least one fan or pump, while in other embodiments, it can be positioned downstream of at least one fan or pump. Additionally, the filtration device may be installed inside the housing 3 of the ozone disinfection device 1. In certain cases, the filtration device may be combined with at least one fan or pump to form a separate component, which can be located outside the housing 3 for operation. Furthermore, the ozone distribution pipeline 22 within the ozone operation system 2 is configured as the conduit for delivering ozone gas in the ozone disinfection device 1. It is configured to communicate with at least the ozone generator 21 and the at least one ozone outlet 35. At least part of the ozone distribution pipeline 22 is located inside the first chamber 32 formed by the housing 3. Additionally, the process of delivering ozone gas from the ozone generator 21 to the disinfection space and recovering ozone gas from the disinfection space can be accomplished using the same or different pipelines. In some embodiments, the ozone operation system 2 may also include a one-way check valve. This valve works in conjunction with the pipeline and is configured to ensure that ozone gas flows in the intended direction, preventing ozone leakage into the external environment outside the housing 3 of the ozone disinfection device 1.

Figure 14:
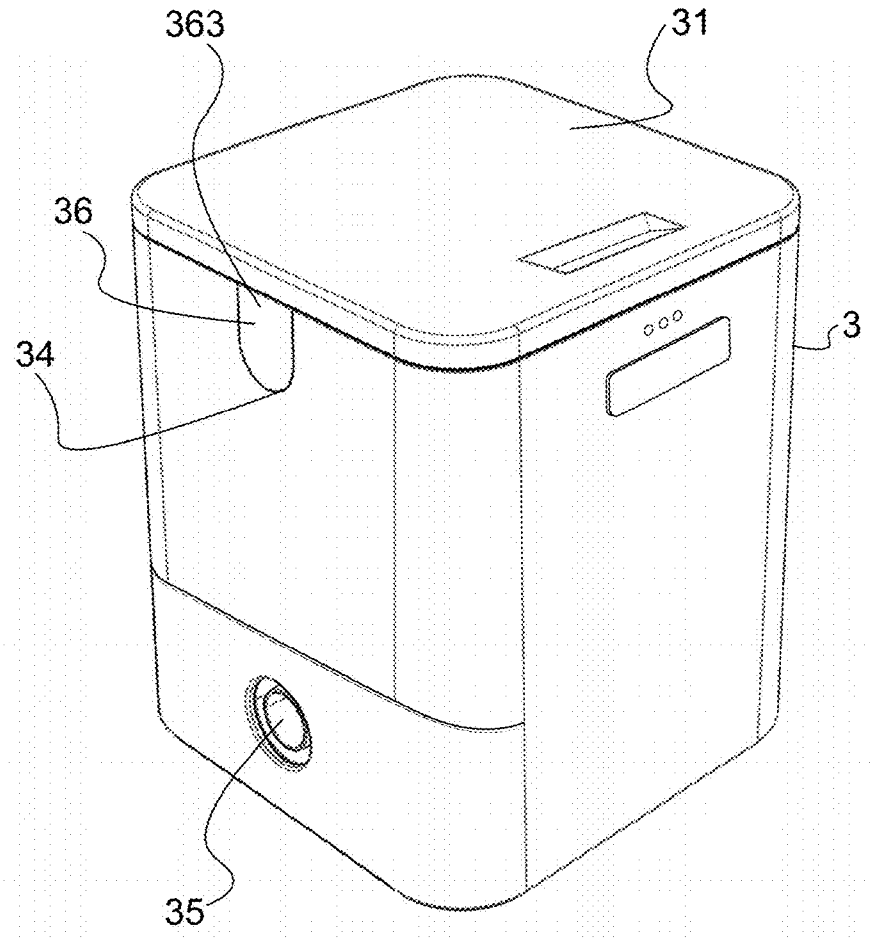
FIG. 14 is a schematic diagram illustrating one form of the receiving slot and its match with the joint component when the joint component is in the first state, in accordance with an embodiment of the present disclosure.

The housing 3 also includes at least one receiving slot 34 and at least one ozone outlet 35. The at least one ozone outlet 35 is connected to the chamber within the housing 3 that houses the ozone operation system 2 and is in communication with at least one component of the ozone operation system 2. In this disclosure, the at least one ozone outlet 35 is specifically connected to the ozone generator 21. At the other end of the at least one ozone outlet 35, it is configured to connect either to one end of a hose or directly to breathing-related equipment. The hose can be understood as any conduit capable of transporting gas and may take any form. In one embodiment, the at least one ozone outlet 35 is configured to connect to the housing 3. The at least one receiving slot 34 is located on at least one of the housing walls 31 and is defined by at least one of the housing walls 31. The term "defined" here can be understood as size limitation, meaning that the size of the receiving slot 34 is determined by the opening in the at least one of the housing walls 31. The at least one receiving slot 34 is configured to interact with a joint component 36 and to work together to form a seal during the operation of the ozone disinfection device 1. The at least one receiving slot 34 has two states: a fully sealed first state and an open second state for receiving a hose (as shown in FIG. 14, which illustrates the fully sealed state of the ozone disinfection device 1). The housing 3 also includes at least one exhaust port 37. In general, the exhaust port 37 is configured to connect to the disinfection space and the filtration device, allowing filtered ozone gas to be discharged into the external environment after passing through the filtration device.

In this disclosure, during the operating period of the ozone disinfection device 1, the volume of ozone gas produced by the ozone generator 21 is sufficient to ensure that the ozone concentration within the disinfection space is not lower than the level required to kill common pathogens found inside respiratory-related equipment and its accessories. This ensures that all bacteria and viruses within the respiratory-related equipment and accessories can be completely eliminated. These accessories include, but are not limited to, masks, nasal masks, hoses, and frames used in conjunction with respiratory-related equipment. Additionally, it ensures that the extraction volume of at least one fan or pump within the ozone operation system 2 is not less than the ozone gas volume produced by the ozone generator 21. This guarantees that the ozone gas within the disinfection space can be completely converted into harmless gases by the filtration device, preventing harm to humans or the environment.

The following section will describe several structural configurations of the ozone disinfection device 1 using specific embodiments.

Embodiment 1

The ozone disinfection device 1 in this embodiment includes an ozone operation system 2, which includes an ozone generator 21 and an ozone distribution pipeline 22, configured to generate ozone gas and control its flow. The device also features a housing 3 composed of multiple housing walls. The housing 3 includes at least one receiving slot 34 and at least one ozone outlet 35. The at least one receiving slot 34 is defined by at least one of the housing walls 31 and/or a joint component 36, with the joint component 36 providing a seal for the at least one receiving slot 34. The ozone operation system 2 also includes at least one fan or pump, configured to expel and/or draw ozone gas.

Figure 8:
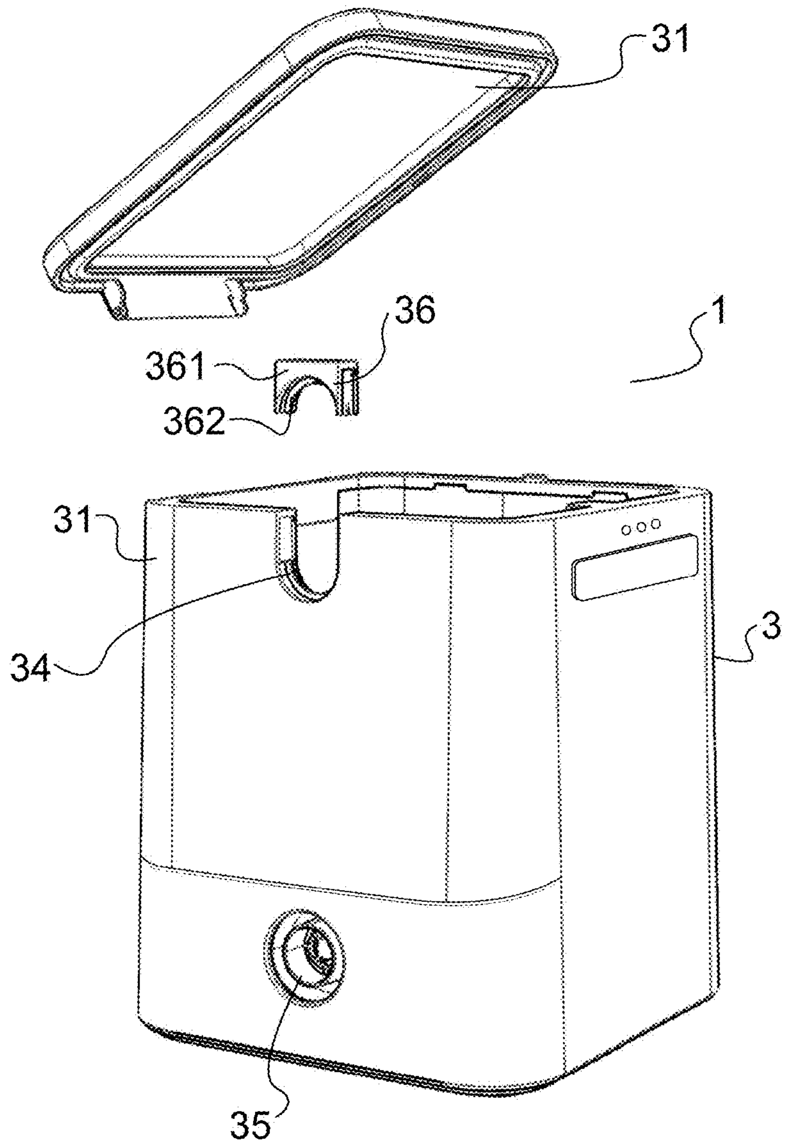
FIG. 8 is a schematic diagram showing one form of the receiving slot and its match with the joint component when the joint component is in the second state, in accordance with an embodiment of the present disclosure.
Figure 9:
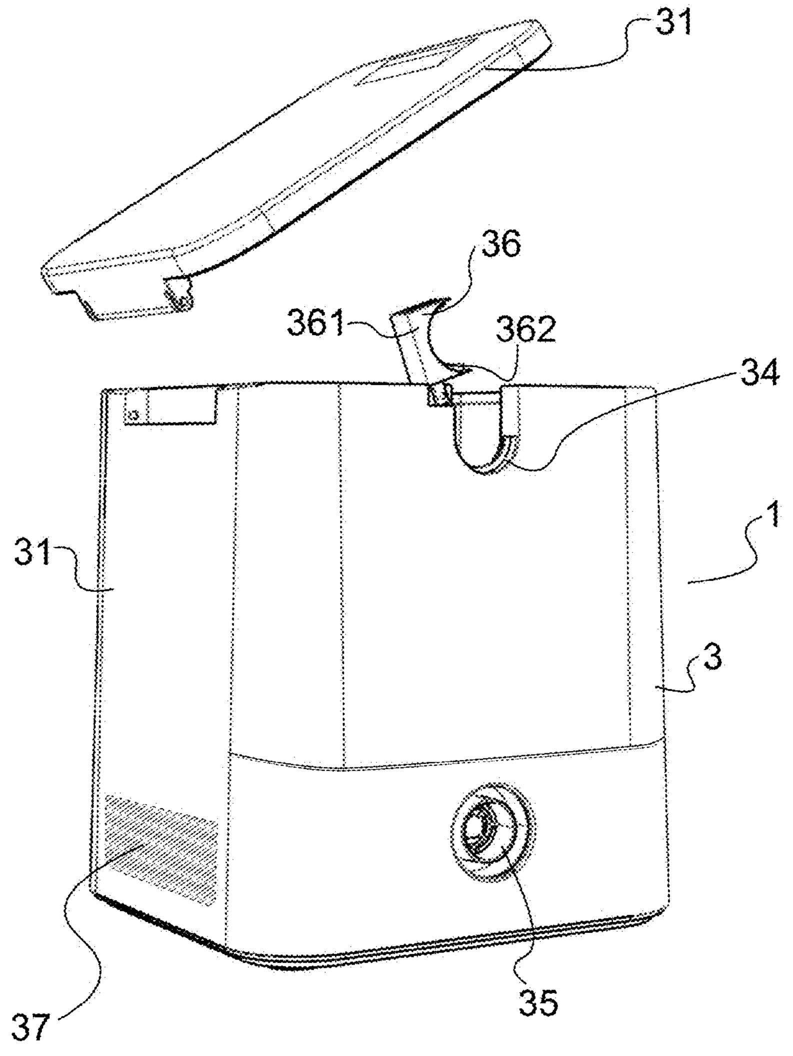
FIG. 9 is a schematic diagram showing another form of the receiving slot and its match with the joint component when the joint component is in the second state, in accordance with an embodiment of the present disclosure.
Figure 11:
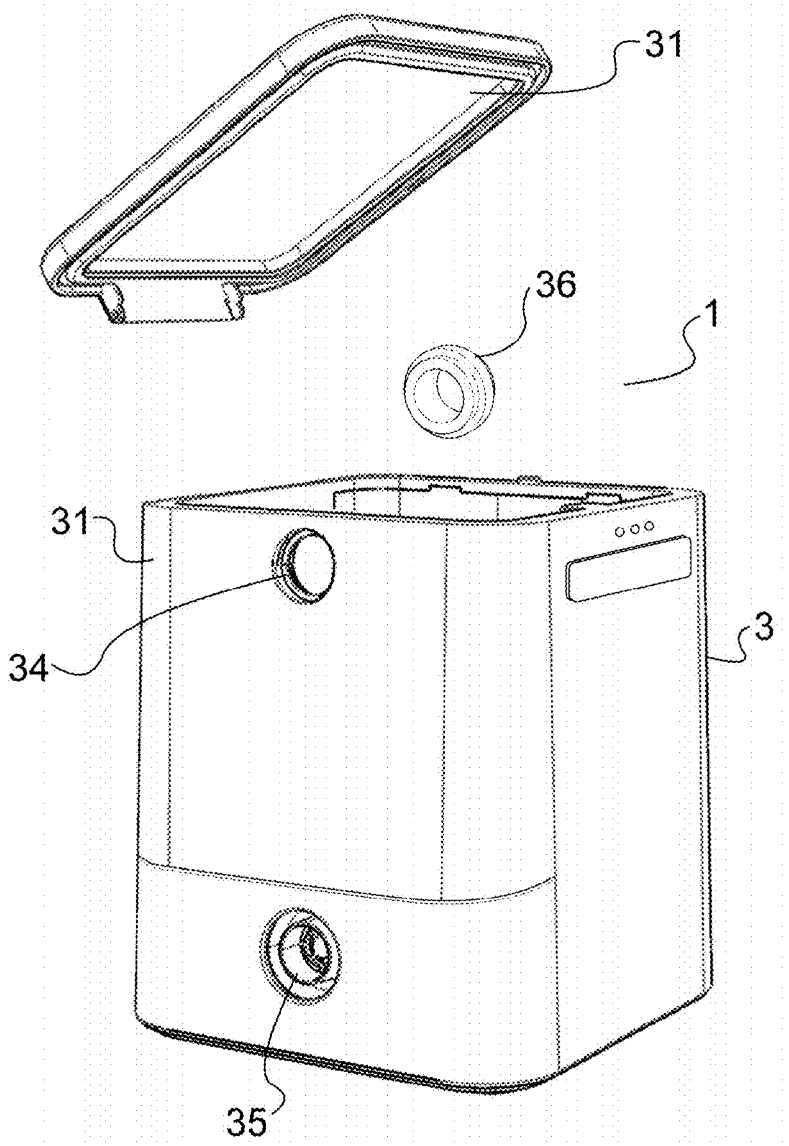
FIG. 11 is a schematic diagram illustrating another form of the receiving slot and its match with the joint component when the joint component is in the second state, in accordance with an embodiment of the present disclosure.
Figure 12:
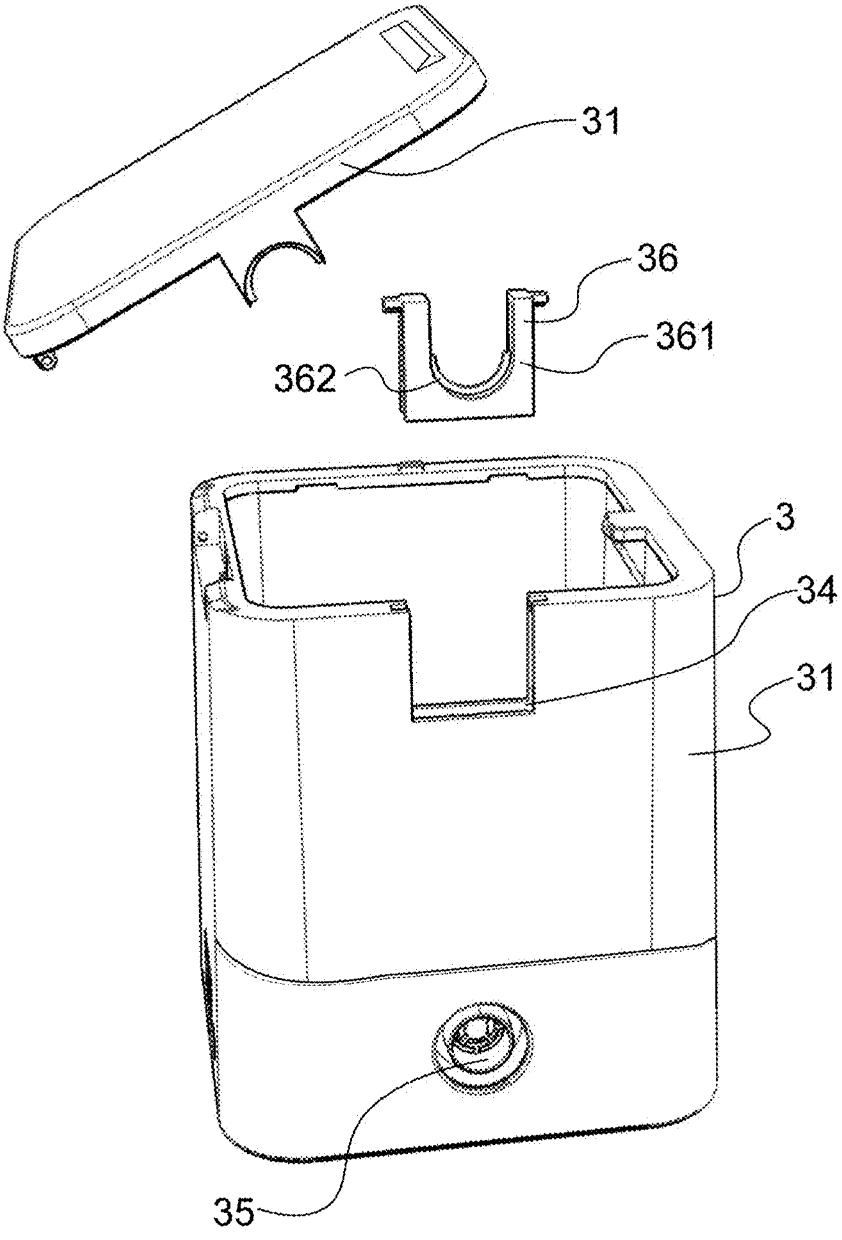
FIG. 12 is a schematic diagram illustrating another variation of the receiving slot and its match with the joint component when the joint component is in the second state, in accordance with an embodiment of the present disclosure.
Figure 13:
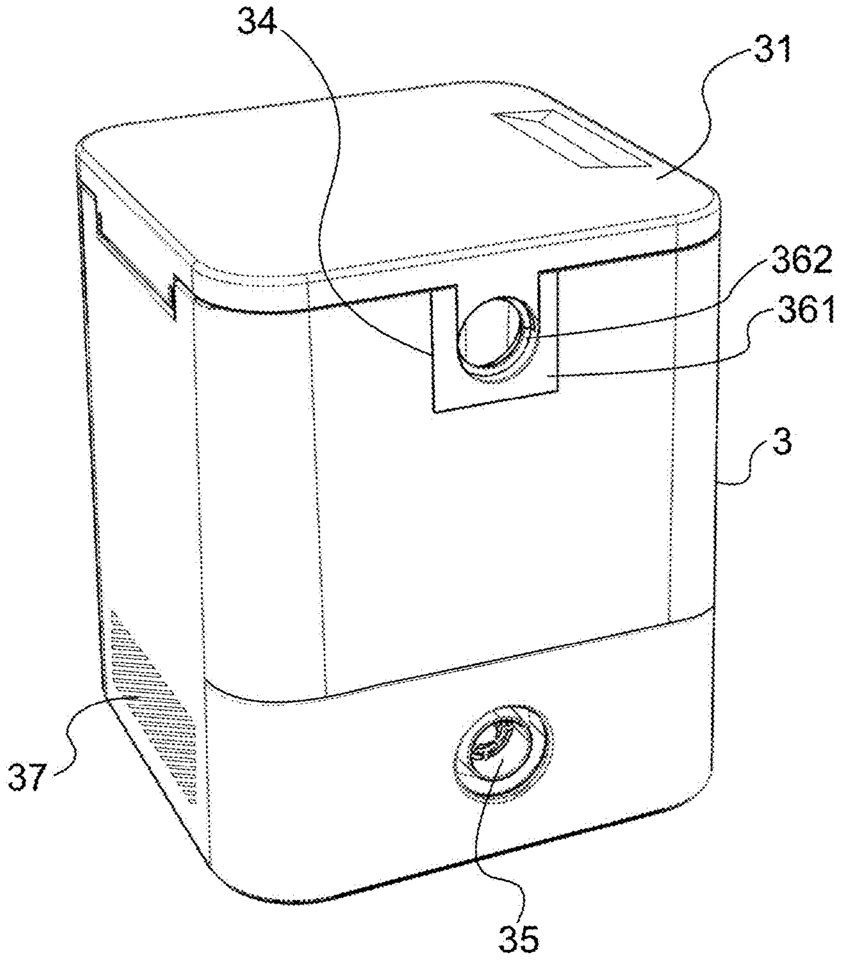
FIG. 13 is a schematic diagram showing the combined configuration of an ozone disinfection device in the form described in FIG. 12, in accordance with an embodiment of the present disclosure.

The joint component 36 and the at least one receiving slot 34 work together as a distinctive structural feature of this disclosure, ensuring an improved seal for the ozone disinfection device 1. This design enhances the device's usability and environmental compatibility. The at least one receiving slot 34 is configured to either connect to one end of a hose or remain sealed (as shown in FIGS. 3 and 14). The joint component 36 includes at least one clipping surface 361 that interfaces with at least one of the housing walls 31 and is connected to at least one sealing element. The at least one sealing element includes a first sealing element 362 and a second sealing element 363. In the ozone disinfection device 1, the first sealing element 362 or the second sealing element 363 can be selected based on different operating states. The first sealing element 362 is used in the first state, a fully sealed state without an opening, while the second sealing element 363 is used in the second state, which accommodates an opening while maintaining a seal. When the joint component 36 engages with the at least one receiving slot 34, the at least one receiving slot 34 has either a first sealing state or a second sealing state. The first sealing state is a fully closed state without an opening, while the second sealing state is configured to seal while accommodating a hose. When the at least one receiving slot 34 is in the second state, the joint component 36 can take one of the following two forms. In the first form, the at least one receiving slot 34 is defined by both the joint component 36 and at least one of the housing walls 31, which work together to seal the hose. In this implementation, the at least one of the housing walls 31 and the joint component 36 cooperate to form an opening for accommodating the hose. The hose is secured and sealed on all sides by both the at least one of the housing walls 31 and the joint component 36 (as shown in FIGS. 8 and 9, which illustrate two examples of this sealing state but are not limited to these forms). In this implementation, the housing walls 31 also include at least one sealing element to complement the joint component 36 in sealing the hose. In the second form, the hose is entirely sealed by the joint component 36, which alone forms an opening to accommodate the hose (as shown in FIGS. 11-13, which demonstrate two examples of this implementation but are not limited to these forms). In FIG. 11, for instance, the joint component 36 is made entirely of soft rubber and connects to an opening in the housing 2 to seal the hose. Regardless of the form, the joint component 36 always interfaces with the housing wall 31. This interface is specifically configured with complementary shapes, ensuring a connection between the joint component 36 and the housing walls 31.

Figure 10:
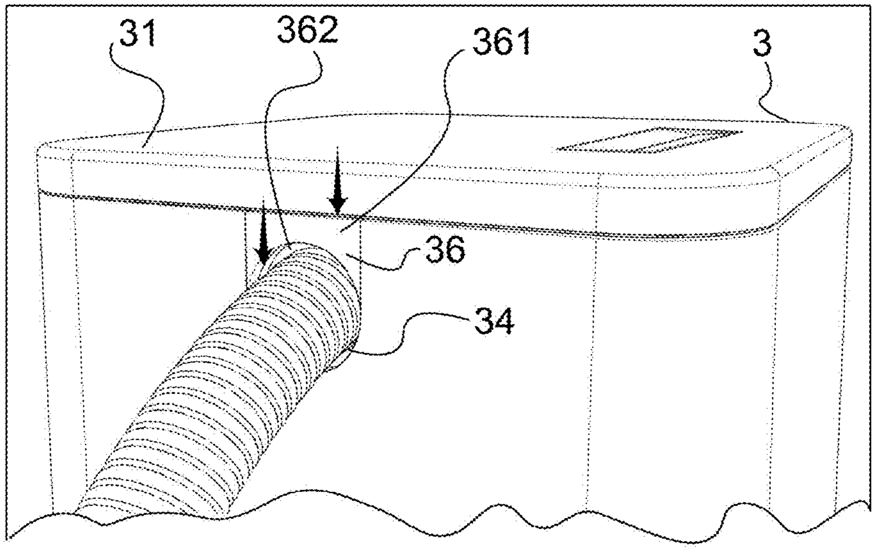
FIG. 10 is a detailed schematic diagram showing one form of the receiving slot when the joint component is in the second state, in accordance with an embodiment of the present disclosure.
Figure 15A:
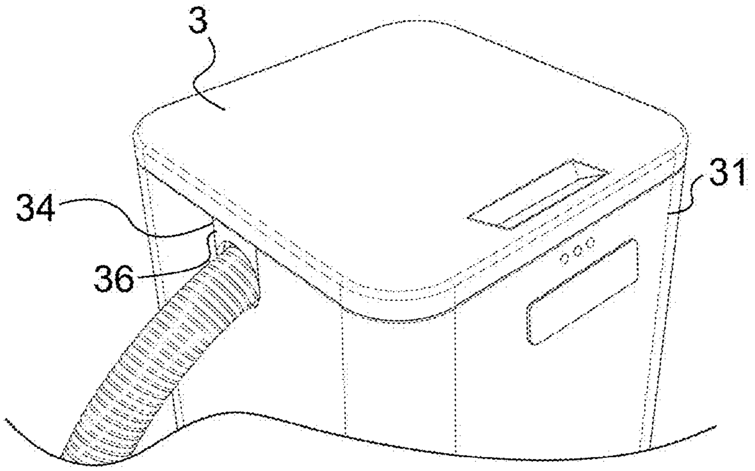
FIGS. 15A and 15B are schematic diagrams illustrating an ozone disinfection device used with different hoses by adjusting and matching with various joint components, in accordance with an embodiment of the present disclosure.
Figure 15B:
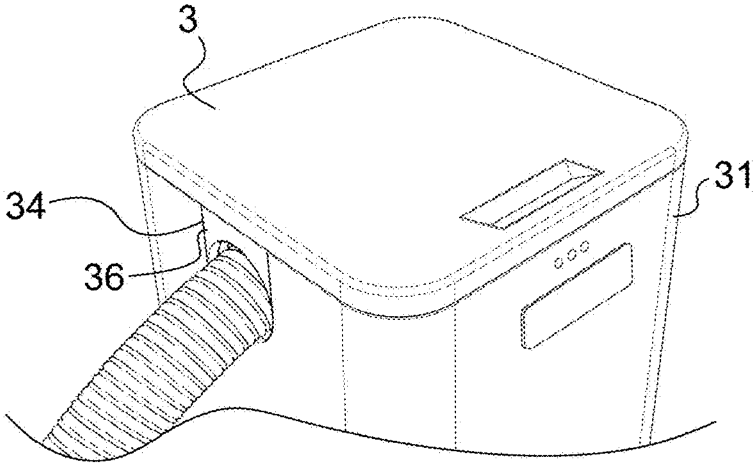

In this implementation, the hose is sealed more tightly, configured to ensure that the hose is not only sealed with the joint component 36 but also further compressed by the upper cover. This enhances the stability of the connection between the at least one receiving slot 34 and the hose's opening while reducing the risk of seal failure or instability caused by repeated use (as shown in FIG. 10). This approach also allows the joint component 36 to be modularized. Specifically, this modularization enables the same ozone disinfection device 1 to use different forms of the joint component 36, allowing the device to connect with hoses of varying diameters. This increases the adaptability and expandability of the ozone disinfection device 1 (as shown in FIGS. 15A and 15B).

Figure 19:
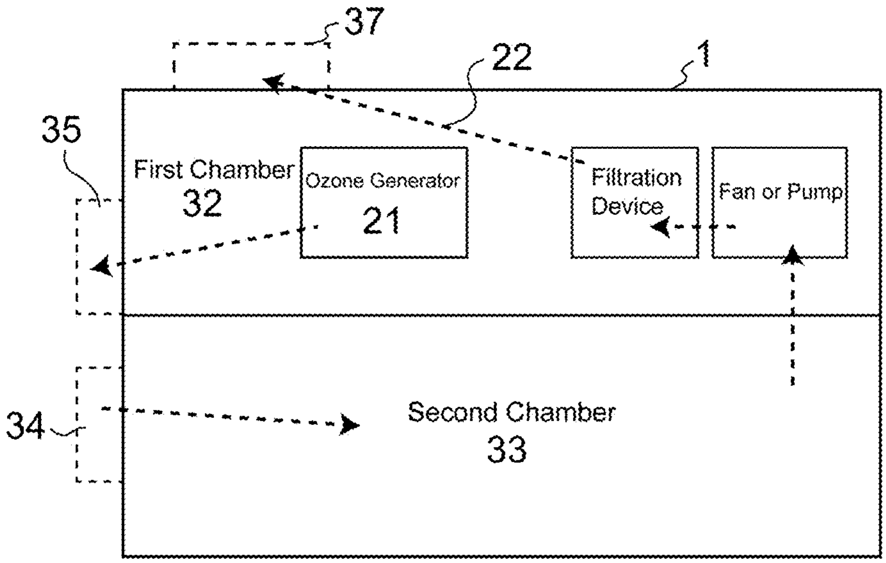
FIG. 19 is a schematic diagram showing one configuration of internal components and gas pathways within an ozone disinfection device, in accordance with an embodiment of the present disclosure.

In this embodiment, the disinfection pathway of the ozone disinfection device 1 operates as follows: the ozone generator 21 within the housing 3 generates ozone gas, which is delivered through the ozone distribution pipeline 22 to the at least one ozone outlet 35. The ozone gas is then transported via a hose connected to the at least one ozone outlet 35 into the disinfection space, where it disinfects respiratory-related equipment or accessories. After disinfection, the gas is recovered by at least one fan or pump and directed back into the housing 3, where it passes through a filtration device. Following filtration and reaction, the gas is expelled through the exhaust port 37 (as shown in FIG. 19). In FIG. 19, the airflow pathway shown is just one example; in this embodiment, the airflow pathway may take various forms, such as passing through the filtration device before reaching the at least one fan or pump.

In some implementations, the ozone disinfection space may not be part of the housing 3 but rather a separate component isolated from the housing 3. The material of this separate component may either be the same as or different from that of the housing 3. In that case, the filtration device and at least one fan or pump are connected to and interact with the separate ozone disinfection space.

Embodiment 2

This embodiment of the ozone disinfection device 1 includes an ozone operation system 2, comprising an ozone generator 21 and an ozone distribution pipeline 22, configured to generate ozone gas and control its flow. The housing 3, composed of multiple housing walls 31, forms at least two chambers and further includes at least one receiving slot 34 and at least one ozone outlet 35. The receiving slot 34 is at least defined by a joint component 36. The two chambers include a first chamber and a second chamber. The ozone operation system 2 is located in the first chamber 32 formed by the housing 3 and further includes at least one fan or pump configured to expel ozone gas from the first chamber 32 and/or draw ozone gas into the first chamber 32.

This embodiment differs from the first in that the ozone outlet 35 is in communication with both the ozone distribution pipeline 22 and the second chamber 33. In this embodiment, the ozone outlet 35 is configured as a three-way pipe 351, which is also configured to connect to the housing. The connection of the ozone outlet 35 to the housing effectively reduces the overall size of the ozone disinfection device 1, allowing the housing of the ozone disinfection device 1 to define its external boundary. This design saves significant space in packaging and transportation of the ozone disinfection device 1, thus reducing costs. The three openings of the three-way pipe 351 are configured to connect a hose or respiratory-related equipment, the ozone generator 21, and a filtration device, respectively. This design integrates multiple openings, reducing the internal pipeline complexity of the ozone disinfection device 1 and enabling a more efficient and straightforward planning of ozone gas flow paths. Additionally, the connection of the ozone outlet 35 to the second chamber 33 facilitates the ozone operation system 2 in the first chamber 32 to achieve quicker and more effective control of ozone gas in the disinfection space. This further simplifies the ozone gas flow path within the ozone disinfection device 1. In this configuration, the ozone outlet 35 can feature multiple openings, such as a three-way pipe 351 or a four-way pipe. These three-way or four-way pipes can also be configured to connect multiple hoses or disinfection spaces, increasing the versatility of the ozone disinfection device 1 and enhancing its disinfection efficiency.

In other implementations, the at least one ozone outlet 35 is not in communication with the second chamber 33.

Figure 17:
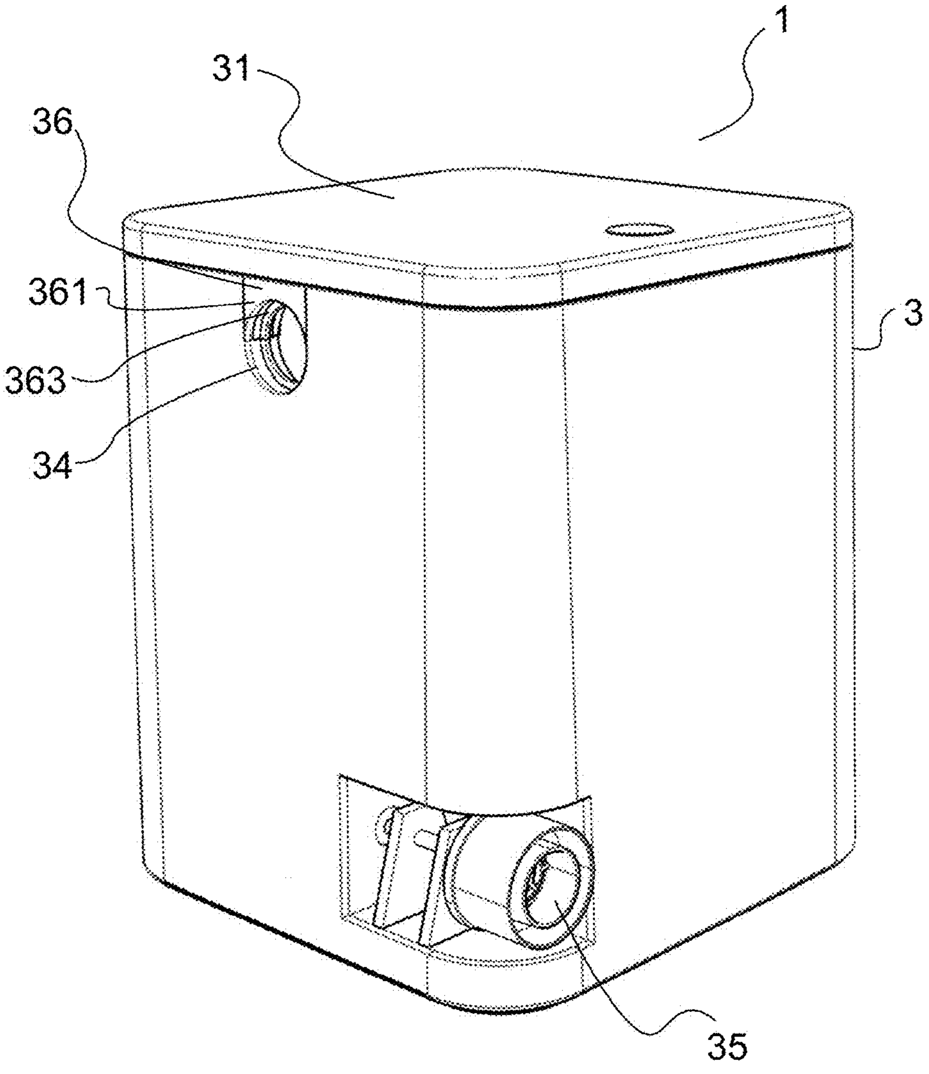
FIG. 17 is a schematic diagram illustrating the ozone outlet of an ozone disinfection device disconnected from the housing, in accordance with multiple embodiments of the present disclosure.

In additional implementations, the ozone outlet 35 is provided outside the housing of the ozone disinfection device 1, configured to connect to a hose or respiratory-related equipment. In this configuration, the ozone outlet 35 passes through the housing 3 (as shown in FIG. 17).

Embodiment 3

This embodiment of the ozone disinfection device 1 includes an ozone operation system 2, comprising an ozone generator 21 and an ozone distribution pipeline 22, configured to generate ozone gas and control its flow. The housing 3, composed of multiple housing walls 31, forms at least two chambers and further includes at least one receiving slot 34 and at least one ozone outlet 35. The receiving slot 34 is at least defined by a joint component 36. The ozone operation system 2 is provided in the first chamber 32 formed by the housing 3 and further includes at least one fan or pump configured to expel ozone gas from the first chamber 32 and/or draw ozone gas into the first chamber 32.

Figure 18:
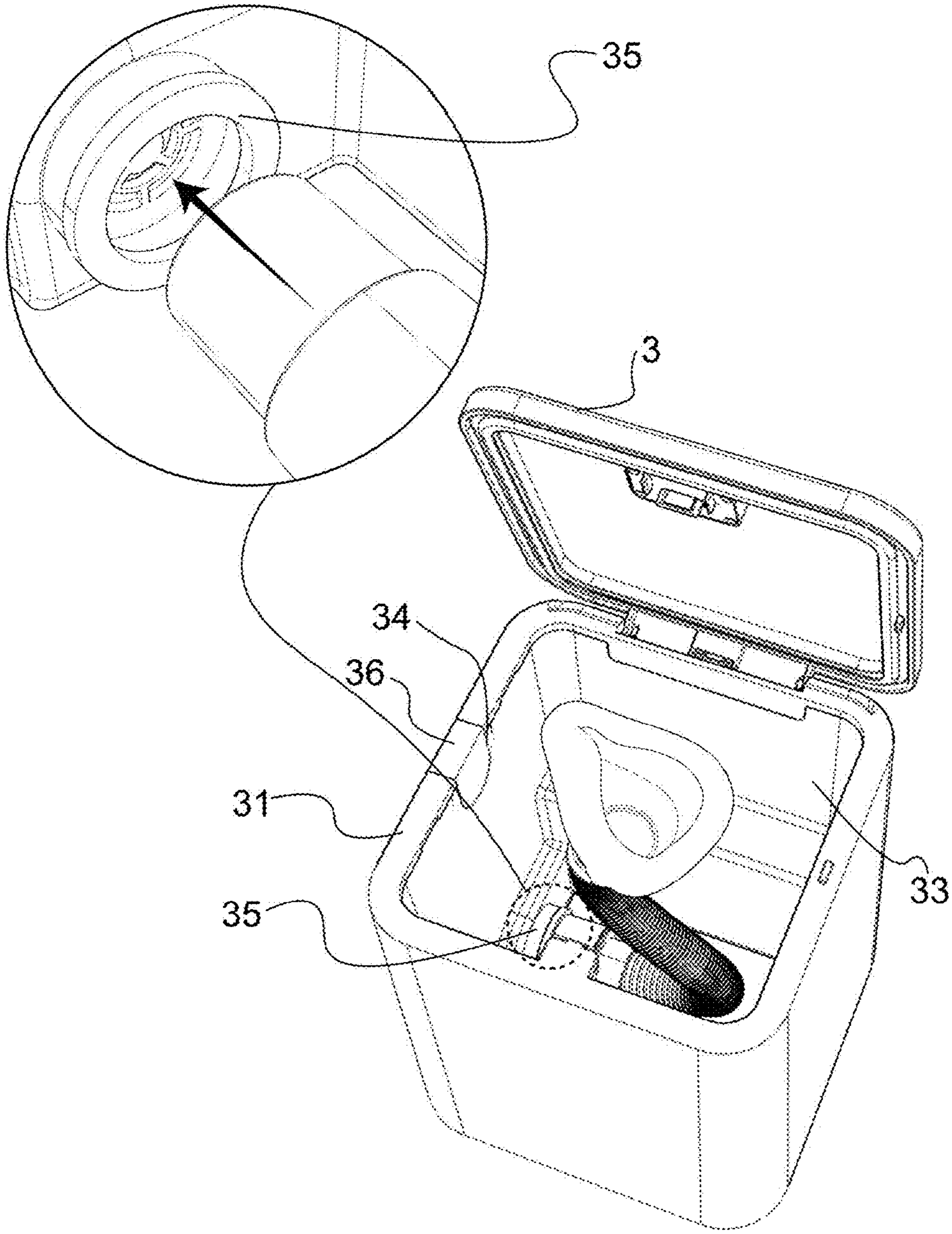
FIG. 18 is a schematic diagram illustrating the extension of the ozone outlet extending to and connecting to the disinfection space in an ozone disinfection device, in accordance with an embodiment of the present disclosure.

This embodiment differs from the first in that the ozone outlet 35 on the housing 3 directly leads to the disinfection space. In this implementation, the ozone gas flow path of the ozone disinfection device 1 is as follows: the ozone generator 21 produces ozone gas, which is transported via the ozone operation system 2 to the ozone outlet 35, and then directly enters the disinfection space (as shown in FIG. 18). In this embodiment, the hose connected to the ozone outlet 35 is configured to remain within a sealed disinfection space, preventing contact between the hose and the external environment. This design facilitates comprehensive disinfection of the hose and effectively reduces the influence of potential contaminants from the external environment on the device to be disinfected. As a result, this implementation enhances both the disinfection efficiency and the safety of the ozone disinfection device 1.

Embodiment 4

This embodiment of the ozone disinfection device 1 includes an ozone operation system 2, comprising an ozone generator 21 and an ozone distribution pipeline 22, configured to generate ozone gas and control its flow. The housing 3, composed of multiple housing walls 31, forms at least two chambers and further includes at least one receiving slot 34 and at least one ozone outlet 35. The receiving slot 34 is at least defined by a joint component 36. The ozone operation system 2 is provided in the first chamber 32 formed by the housing 3 and further includes at least one fan or pump configured to expel ozone gas from the first chamber 32 and/or draw ozone gas into the first chamber 32. Additionally, the ozone operation system 2 includes at least one ozone sensor.

Figure 20:
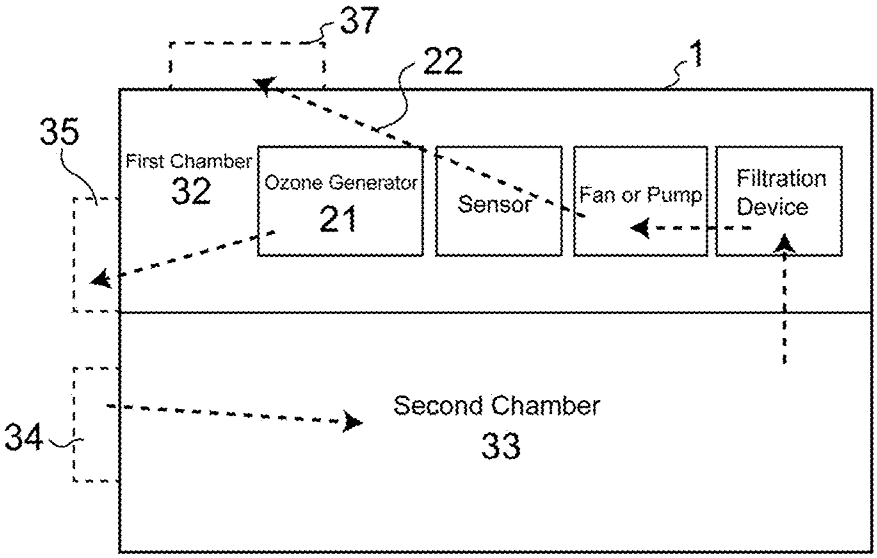
FIG. 20 is a schematic diagram showing one configuration of internal components and gas pathways within the ozone disinfection device, in accordance with an embodiment of the present disclosure.

This embodiment differs from the first in that the ozone disinfection device 1 in this embodiment includes at least one ozone sensor (as shown in FIG. 20). The at least one ozone sensor can be provided anywhere within the ozone disinfection device 1. In FIG. 20, the depicted airflow path is just one example; in this embodiment, the airflow path may vary, such as passing through the fan or pump before reaching the filtration device. The at least one ozone sensor is configured to monitor the concentration of ozone gas in various parts of the ozone disinfection device 1 in real-time. This ensures that the ozone gas concentration produced by the ozone generator 21 remains within a safe range, preventing potential health or environmental hazards due to malfunctioning of the ozone operation system 2. Furthermore, the at least one ozone sensor can interact with other components in the ozone operation system 2, such as the ozone generator 21, to allow for user-adjustable intelligent ozone concentration output. This provides users with greater operational flexibility while reducing waste of energy or consumables, improving the safety and reliability of the device, and enhancing user confidence in the product.

In other implementations, the ozone operation system 2 may include additional sensors of various types, including but not limited to temperature and humidity sensors, pressure sensors, oxygen sensors, flow sensors, volatile organic compound sensors, particulate matter sensors, ultraviolet sensors, current sensors, or safety lock sensors.

Embodiment 5

This embodiment of the ozone disinfection device 1 includes an ozone operation system 2, comprising an ozone generator 21 and an ozone distribution pipeline 22, configured to generate ozone gas and control its flow. The housing 3, composed of multiple housing walls 31, forms at least two chambers and further includes at least one receiving slot 34 and at least one ozone outlet 35. The receiving slot 34 is at least defined by a joint component 36. The ozone operation system 2 is provided in the first chamber 32 formed by the housing 3 and further includes at least one fan or pump configured to expel ozone gas from the first chamber 32 and/or draw ozone gas into the first chamber 32.

This embodiment differs from the first in that the ozone operation system 2 also includes an alarm function. The alarm is configured to notify the user visually or audibly when the device malfunctions or when it is not being used according to the specified instructions, thereby preventing potential greater harm. The alarm system typically functions in conjunction with at least one ozone sensor to significantly enhance the intelligence of the ozone disinfection device 1. When a malfunction occurs, the alarm system can interact with other components of the ozone operation system 2 to quickly identify and pre-process the problem area, preventing further serious damage caused by continued operation. This functionality also facilitates maintenance personnel in locating and addressing issues during repairs. The alarm system enhances user safety, optimizes user experience, and ensures that the device performs its disinfection functions more effectively and reliably. The alarm system can also work in tandem with the user interface to provide reminders or notifications to users.

Additionally, the technical features described in this and the previous embodiments may be combined as needed to produce an ozone disinfection device 1 that includes all or some of these features.

The ozone disinfection device 1 described in this disclosure provides several notable benefits.

1. Ozone disinfection device 1 is particularly crucial for respiratory-related equipment. Prolonged use of such equipment without regular disinfection or cleaning allows pathogens and bacteria to proliferate rapidly. These microorganisms can enter the human body through the device, posing significant health risks. For devices that require extended and frequent use, periodic disinfection of both the equipment and its accessories is necessary to ensure safe operation. As the demand for respiratory-related equipment increases, the need for compatible ozone disinfection devices 1 will also grow. This disclosure introduces a novel design for ozone disinfection devices, offering users more diversified options. Ozone was selected as the primary disinfection method in this disclosure because of its broad-spectrum sterilization capabilities. Ozone can effectively eliminate a wide range of bacteria, viruses, fungi, and other microorganisms, as well as decompose harmful gases and eliminate odors. This makes ozone highly effective in various scenarios. Compared to other disinfection methods on the market, such as high-temperature or ultraviolet (UV) disinfection, ozone has distinct advantages. High-temperature disinfection requires stringent thermal resistance in device housing to prevent heat damage to internal components, increasing material and design complexity. UV disinfection, on the other hand, is limited by physical obstructions; for effective disinfection, the device must be transparent and free of barriers, which compromises its aesthetics and structural design. Ozone disinfection, by contrast, does not require heating or depend on unobstructed surfaces—only proper sealing is needed for effective operation. This disclosure's ozone disinfection device 1 not only meets users' daily disinfection needs but also surpasses existing devices in terms of sealing performance, enhanced safety, simplified structure, and reduced costs. By addressing current market demands and incorporating innovative design features, this disclosure aims to provide users with a more flexible, convenient, and safe disinfection experience. Further details will be elaborated upon below.

2. This disclosure improves the sealing performance of the receiving slot 34 in the ozone disinfection device 1, making it more secure and stable. By introducing the joint component 36 as a specialized part, the receiving slot 34 is no longer directly sealed with the upper cover of the ozone disinfection device 1. Instead, it is defined and/or sealed via at least the joint component 36. This design differs from existing devices on the market where the receiving slot 34 directly interacts with the upper cover for sealing. It reduces the risk of sealing failure or instability caused by the frequent movement of the upper cover. When the receiving slot 34 is configured to secure one end of a hose, the sealing of the opening between the receiving slot 34 and the hose is not only achieved by the joint component 36 but is also further compressed by the upper cover on the exterior of the joint component 36. This approach ensures the stability of the connection between the receiving slot 34 and the hose opening. Separating the frequently used components and components for joining, from other components offers additional benefits. When the seal at the opening fails due to prolonged use or other reasons, the issue can be resolved by directly replacing the joint component 36 without needing to replace the upper cover or other integral components. This design makes the ozone disinfection device 1 easier to maintain and reduces maintenance costs. Furthermore, this method avoids issues related to the upper cover extending into a slender end at the hose connection, which is prone to damage and difficult to seal. Sealing through the joint component 36 instead of directly using the upper cover also enables modularity for the receiving slot 34. Modularity allows users to select different joint components 36 to accommodate hoses of varying diameters, depending on their needs or the specifications of the device or accessory being disinfected. For manufacturers and retailers, this modular design simplifies inventory management. Different specifications of the joint component 36 can be sold individually or as part of a set to meet diverse user requirements. This design not only offers users a wider range of options but also opens up diversified sales models, enhancing flexibility in both use and distribution.

3. This disclosure equips the ozone disinfection device 1 with a safety system to prevent the overproduction of ozone, which could harm the environment or user health, while adhering to the principles of green design. As a strong oxidant, it is critical to minimize ozone leakage and secondary pollution. High concentrations of ozone can irritate or damage the respiratory tract, eyes, and skin, and prolonged exposure to ozone levels exceeding 0.1 ppm may lead to respiratory system damage. By incorporating a safety system, this disclosure effectively reduces the potential risks of ozone to both the environment and users. Specifically, the ozone disinfection device 1 is configured to ensure that when the upper cover is in a non-closed state, the fan or pump does not operate. This prevents ozone leakage and avoids exposing users or the external environment to high concentrations of ozone gas. In some embodiments, the device also includes at least one sensor to monitor the ozone concentration in real time. If the detected ozone concentration exceeds the preset safe range, the ozone disinfection device 1 will immediately cease operation and may even trigger an alarm to alert the user. Additionally, the safety system can include extra sensors such as temperature and humidity sensors, oxygen concentration sensors, or current sensors. These sensors ensure that the ozone disinfection device 1 operates under optimal conditions, further enhancing its safety features and providing protection for both users and the environment.

4. This disclosure also proposes connecting the ozone distribution pipeline 22 with the ozone outlet 35 and the second chamber 33, enabling more precise control of ozone gas and improving the efficiency of the ozone disinfection device 1. This implementation optimizes the delivery and recovery routes of ozone gas, achieving high disinfection efficiency with the shortest path. Integrating multiple outlets further streamlines the structure of the ozone disinfection device 1. Compared to existing ozone disinfection devices on the market, this design not only enhances operational efficiency but also significantly improves the overall structure of the device. It reduces the use of complex components and simplifies installation steps, thereby maximizing production efficiency. Additionally, this design substantially lowers the manufacturing and assembly costs of the ozone disinfection device 1, making it more suitable for large-scale mass production. By using a single three-way pipe to connect the ozone distribution pipeline 22 and the disinfection space, this disclosure reduces the number of pipe connections and minimizes potential leakage risks, thereby enhancing the device's stability and safety. Furthermore, this design facilitates the maintenance and upgrading of the ozone disinfection device 1, offering users a more convenient and reliable experience.

The technical features described in the above embodiments can be combined in various ways. For simplicity, all possible combinations of the technical features in these embodiments have not been explicitly described. However, as long as there are no contradictions between the combinations of these features, they should be considered within the scope of this specification.

The above embodiments represent specific implementations of this disclosure. While the descriptions are detailed and specific, they should not be interpreted as limiting the scope of the patent. It should be noted that those skilled in the art may make various modifications and improvements without departing from the spirit of this disclosure. All such variations and modifications fall within the scope of this disclosure as defined by the appended claims.

It must be noted that as used herein and in the appended claims, the singular forms "a", "an", and "the" include their plural equivalents, unless the context clearly dictates otherwise.

The invention claimed is:

1. An ozone disinfection device configured to connect with a hose or respiratory-related equipment for disinfection, comprising:

an ozone operation system that includes an ozone generator and an ozone distribution pipeline, configured to generate ozone gas and control a flow of the ozone gas; and a housing formed by a plurality of housing walls, wherein the housing is configured to form at least two chambers and further includes at least one receiving slot and at least one ozone outlet;

wherein the at least one receiving slot is configured to be defined by at least one of the housing walls and a joint component, and the joint component is configured to provide a seal for the at least one receiving slot by being configured to be compressible by an upper cover of the ozone disinfection device;

wherein the at least two chambers include a first chamber and a second chamber, and the ozone operation system is configured to be provided in the first chamber and is in communication with the second chamber;

wherein the at least one ozone outlet is in communication with both the ozone distribution pipeline and the second chamber; and wherein the ozone disinfection device is configured in a way such that the ozone gas generated by the ozone generator after disinfection is recycled back into the housing through a fan or pump, wherein the fan or pump is configured to expel and/or draw the ozone gas.

2. The ozone disinfection device according to claim 1, wherein the at least one ozone outlet is configured to connect to the housing.

3. The ozone disinfection device according to claim 1, wherein the at least one receiving slot has a first sealing state or a second sealing state, wherein the first sealing state is configured to be closed without an opening, and the second sealing state is configured to be sealed while accommodating a hose.

4. The ozone disinfection device according to claim 1, wherein the joint component includes at least one sealing element, and the at least one sealing element comprises a first sealing element and a second sealing element.

5. The ozone disinfection device according to claim 1, wherein the ozone operation system further includes at least one ozone sensor.

6. An ozone disinfection device configured to connect with a hose or respiratory-related equipment for disinfection, comprising:

an ozone operation system that includes an ozone generator and an ozone distribution pipeline, configured to generate ozone gas and control a flow of the ozone gas, wherein the ozone operation system also comprises ozone gas recovery; and a housing formed by a plurality of housing walls, wherein the housing further includes at least one receiving slot and at least one ozone outlet;

wherein the at least one receiving slot is configured to be defined by at least one of the housing walls and a joint component, and the joint component is configured to include at least one sealing element;

wherein the ozone operation system further includes a fan or pump, and the fan or pump being configured to expel and/or draw the ozone gas;

wherein the ozone operation system further comprises a filtration device; and wherein the ozone disinfection device is configured in a way such that the ozone gas generated by the ozone generator after disinfection is recycled back into the housing passes through the fan or pump to the filtration device for decomposition after disinfection, and wherein the fan or pump is configured to control a flow direction of the ozone gas.

7. The ozone disinfection device according to claim 6, wherein a state of the fan or pump differs depending on whether the ozone disinfection device is in an open or closed state.

8. The ozone disinfection device according to claim 7, wherein the fan or pump does not operate when the ozone disinfection device is in a non-closed state.

9. The ozone disinfection device according to claim 6, wherein the at least one sealing element include a first sealing element and a second sealing element, and wherein the ozone disinfection device is configured to selectively use the first sealing element or the second sealing element depending on its operating state.

10. The ozone disinfection device according to claim 6, wherein at least one of the housing walls and the joint component are configured to form an opening to accommodate the hose.

11. The ozone disinfection device according to claim 6, wherein the ozone operation system further includes at least one ozone sensor.

12. The ozone disinfection device according to claim 6, wherein the housing is configured to form at least two chambers.

13. An ozone disinfection device configured to connect with a hose or respiratory-related equipment for disinfection, comprising:

an ozone operation system that includes an ozone generator and an ozone distribution pipeline, configured to generate ozone gas and control a flow of the ozone gas, wherein the ozone operation system also comprises ozone gas recovery; and a housing formed by a plurality of housing walls, wherein the housing is configured to form at least two chambers and further includes at least one receiving slot and at least one ozone outlet;

wherein the at least one receiving slot is defined by a joint component;

wherein the at least two chambers include a first chamber, the ozone operation system being provided in the first chamber, wherein the ozone operation system further includes a fan or pump configured to expel the ozone gas from the first chamber and/or draw ozone gas into the first chamber, and wherein the ozone operation system further comprises a filtration device; and wherein the ozone disinfection device is configured in a way such that the ozone gas generated by the ozone generator after disinfection is recycled back into the housing through the fan or pump to the filtration device for decomposition after disinfection, and wherein the fan or pump is configured to control a flow direction of the ozone gas.

14. The ozone disinfection device according to claim 13, wherein the housing walls further include at least one sealing element configured to seal the hose in conjunction with the joint component.

15. The ozone disinfection device according to claim 13, wherein the at least one ozone outlet is in communication with the ozone generator.

16. The ozone disinfection device according to claim 13, wherein the ozone operation system further includes at least one ozone sensor.

17. An ozone disinfection device configured to connect with a hose or respiratory-related equipment for disinfection, comprising:

an ozone operation system that includes an ozone generator and an ozone distribution pipeline, configured to generate ozone gas and control a flow of the ozone gas; and a housing formed by a plurality of housing walls, wherein the housing further includes at least one receiving slot and at least one ozone outlet;

wherein the at least one receiving slot is defined by a joint component and at least one of the housing walls, the housing walls including at least one sealing element;

wherein the joint component includes at least one clipping surface that interfaces with the at least one of the housing walls through the at least one sealing element, the at least one sealing element comprising a first sealing element and a second sealing element, wherein the joint component is configured to provide a seal for the at least one receiving slot by being configured to be compressible by an upper cover of the ozone disinfection device;

wherein the ozone operation system further includes a fan or pump, and the fan or pump being configured to expel and/or draw the ozone gas, and wherein the ozone disinfection device is configured in a way such that the ozone gas generated by the ozone generator after disinfection is recycled back into the housing through the fan or pump.

18. The ozone disinfection device according to claim 17, wherein the at least one ozone outlet is configured to connect to a first end of the hose or directly to the respiratory-related equipment.

19. The ozone disinfection device according to claim 18, wherein the at least one receiving slot is configured to connect to a second end of the hose.

20. The ozone disinfection device according to claim 17, wherein the housing forms at least two chambers.

21. The ozone disinfection device according to claim 16, wherein the ozone disinfection device is configured to selectively use the first sealing element or the second sealing element depending on its operating state.

* * * * *